United States Patent
O'Neill et al.

(10) Patent No.: US 8,060,330 B2
(45) Date of Patent: Nov. 15, 2011

(54) METHOD AND SYSTEM FOR CENTERING WAFER ON CHUCK

(75) Inventors: Robert Griffith O'Neill, Fremont, CA (US); Jorge Luque, Redwood City, CA (US); Shang-I Chou, San Jose, CA (US); Harmeet Singh, Fremont, CA (US)

(73) Assignee: Lam Research Corporation, Fremont, CA (US)

( * ) Notice: Subject to any disclaimer, the term of this patent is extended or adjusted under 35 U.S.C. 154(b) by 406 days.

(21) Appl. No.: 12/334,275

(22) Filed: Dec. 12, 2008

(65) Prior Publication Data

US 2010/0150695 A1  Jun. 17, 2010

(51) Int. Cl.
*G06F 19/00* (2011.01)
*G06F 17/40* (2006.01)

(52) U.S. Cl. ............ 702/105; 438/14; 702/90; 702/187; 702/189

(58) Field of Classification Search ............ 33/501, 33/520; 73/431.1, 865.8; 324/500, 537, 324/757.01, 757.03, 757.04, 757.05; 356/138, 356/153, 614; 382/100, 141, 145, 151; 438/14; 702/1, 33, 35, 36, 85, 90, 94, 95, 105, 127, 702/150, 152, 155, 157, 158, 187, 189
See application file for complete search history.

(56) References Cited

U.S. PATENT DOCUMENTS

| | | | | |
|---|---|---|---|---|
| 2,867,443 A * | 1/1959 | Swanson | ........................ | 279/119 |
| RE24,684 E * | 8/1959 | Swanson | ........................ | 279/119 |
| 2,905,476 A * | 9/1959 | Brainerd | ........................ | 279/116 |
| 3,344,695 A * | 10/1967 | Hohwart | ........................ | 82/165 |
| 3,609,838 A * | 10/1971 | Wiest | ........................ | 29/38 C |
| 3,845,962 A * | 11/1974 | Molin | ........................ | 279/4.04 |
| 5,905,850 A * | 5/1999 | Kaveh | ........................ | 700/259 |
| 6,225,012 B1 * | 5/2001 | Nishi et al. | ........................ | 430/22 |
| 6,405,101 B1 * | 6/2002 | Johanson et al. | ........................ | 700/218 |
| 6,471,464 B1 * | 10/2002 | Fay et al. | ........................ | 414/783 |
| 6,549,290 B2 * | 4/2003 | Miura et al. | ........................ | 356/614 |
| 6,637,737 B1 * | 10/2003 | Beecherl et al. | ........................ | 269/71 |
| 6,906,794 B2 * | 6/2005 | Tsuji | ........................ | 356/237.4 |
| 6,973,370 B2 * | 12/2005 | Ito et al. | ........................ | 700/218 |
| 7,102,743 B2 * | 9/2006 | Tsuji et al. | ........................ | 356/237.2 |
| 7,479,236 B2 * | 1/2009 | Chen et al. | ........................ | 216/59 |
| 7,486,878 B2 * | 2/2009 | Chen et al. | ........................ | 396/5 |
| 7,547,181 B2 * | 6/2009 | Fukatsu et al. | ........................ | 414/757 |
| 7,925,378 B2 * | 4/2011 | Gilchrist et al. | ........................ | 700/218 |
| 7,933,009 B2 * | 4/2011 | Serebryanov et al. | ........................ | 356/213 |
| 7,963,736 B2 * | 6/2011 | Takizawa et al. | ........................ | 414/217 |
| 2001/0006571 A1 * | 7/2001 | Miura et al. | ........................ | 385/52 |
| 2003/0202178 A1 * | 10/2003 | Tsuji et al. | ........................ | 356/237.2 |
| 2005/0016818 A1 * | 1/2005 | Ito et al. | ........................ | 198/345.1 |
| 2005/0062960 A1 * | 3/2005 | Tsuji et al. | ........................ | 356/237.2 |
| 2006/0102289 A1 * | 5/2006 | Fukatsu et al. | ........................ | 156/345.55 |

(Continued)

*Primary Examiner* — Edward Cosimano
(74) *Attorney, Agent, or Firm* — Martine Penilla Group, LLP

(57) ABSTRACT

A wafer handling mechanism is operated to place a wafer on a chuck. A chucking force is then applied to the wafer, whereby wafer support features of the chuck transfer a defect pattern onto a surface of the wafer. The surface of the wafer is analyzed by a defect metrology tool to obtain a mapping of the defect pattern transferred onto the surface of the wafer. A center coordinate of the chuck within a coordinate system of the wafer is determined by analyzing the defect pattern as transferred to the surface of the wafer. A spatial offset between the center coordinate of the chuck and the center of the wafer is determined. The spatial offset is used to adjust the wafer handling mechanism so as to enable alignment of the center of the wafer to the center coordinate of the chuck.

20 Claims, 13 Drawing Sheets

U.S. PATENT DOCUMENTS

| | | | |
|---|---|---|---|
| 2007/0071581 A1* | 3/2007 | Gilchrist et al. | 414/217 |
| 2007/0188859 A1* | 8/2007 | Tokita | 359/394 |
| 2008/0080845 A1* | 4/2008 | Chen et al. | 396/4 |
| 2008/0081383 A1* | 4/2008 | Chen et al. | 438/14 |
| 2009/0027657 A1* | 1/2009 | Serebryanov et al. | 356/73 |
| 2009/0088887 A1* | 4/2009 | Chen et al. | 700/114 |
| 2009/0252580 A1* | 10/2009 | Takizawa et al. | 414/222.02 |
| 2010/0277749 A1* | 11/2010 | Rodnick et al. | 356/623 |

* cited by examiner

METHOD AND SYSTEM FOR CENTERING WAFER ON CHUCK

BACKGROUND

In the fabrication of semiconductor devices such as integrated circuits, memory cells, and the like, a series of manufacturing operations are performed to define features on semiconductor wafers ("wafers" or "substrates"). The wafers include integrated circuit devices in the form of multi-level structures defined on a silicon substrate. At a substrate level, transistor devices with diffusion regions are formed. In subsequent levels, interconnect metallization lines are patterned and electrically connected to the transistor devices to define a desired integrated circuit device. Also, patterned conductive layers are insulated from other conductive layers by dielectric materials.

A number of the various wafer manufacturing operations require handling and placement of the wafer on a chuck within a processing chamber. Such placement of the wafer on the chuck is done remotely using a robotic device. It is generally important that the wafer be placed on the chuck in a known position relative to the chuck. For example, it may be specified that the wafer should be centered within a wafer receiving area of the chuck. However, accuracy in placement of the wafer on the chuck by the robotic device is generally a function of how well the robotic device is calibrated to a spatial position of the chuck. Therefore, the wafer may be placed in a non-centered manner on the chuck due to miscalibration between the robotic device and the spatial position of the chuck. When this occurs, it is not generally known how far off-center the wafer is relative to the wafer receiving area of the chuck.

Processes performed on the wafer in the chamber generally assume that the wafer is centered within the wafer receiving area of the chuck. Therefore, when the wafer is positioned in a non-centered manner on the chuck, it is possible that the wafer fabrication process will suffer in terms of desired results. Consequently, it is of interest to better control centering of the wafer on the chuck.

SUMMARY

In one embodiment, a method is disclosed for centering a wafer on a chuck. The method includes an operation for acquiring defect metrology data from a surface of the wafer having contacted the chuck. The method also includes an operation for determining a center coordinate of the chuck within a coordinate system of the wafer based on the defect metrology data. The method further includes an operation for determining a difference between the center coordinate of the chuck and a center of the wafer. Additionally, a method operation is performed to adjust a wafer handling mechanism based on the determined difference between the center coordinate of the chuck and the center of the wafer, so as to enable alignment of the center of the wafer to the center coordinate of the chuck.

In another embodiment, a method is disclosed for determining an offset of a wafer center from a chuck center. In the method, a wafer is placed on a chuck. The chuck includes a plurality of support features defined to contact a surface of the wafer when placed upon the chuck. A chucking pressure is then applied to the wafer, whereby a defect pattern is transferred by the plurality of support features to the surface of the wafer in contact with the chuck. The wafer is removed from the chuck. The defect pattern on the surface of the wafer is analyzed to locate a center coordinate of the chuck within a coordinate system of the wafer. An offset between the center coordinate of the chuck and a center of the wafer is then determined. The determined offset between the center coordinate of the chuck and the center of the wafer is stored in a computer readable memory.

In another embodiment, a system for centering a wafer on a chuck is disclosed. The system includes a chuck. The chuck includes a plurality of support features defined to contact a surface of a wafer when positioned upon the chuck. The system also includes a wafer handling mechanism defined to position the wafer on the chuck. The system further includes a defect metrology tool defined to detect and map defects on the surface of the wafer. Additionally, the system includes an analysis module defined to determine a center coordinate of the chuck within a wafer coordinate system. The center coordinate of the chuck is determined based on a defect map generated by the defect metrology tool. The defect map represents defects transferred to the surface of the wafer by the plurality of support features of the chuck. The analysis module is further defined to determine an offset between the center coordinate of the chuck and a center of the wafer, and store the determined offset in a computer readable memory.

Other aspects and advantages of the invention will become more apparent from the following detailed description, taken in conjunction with the accompanying drawings, illustrating by way of example the present invention.

DETAILED DESCRIPTION

In the following description, numerous specific details are set forth in order to provide a thorough understanding of the present invention. It will be apparent, however, to one skilled in the art that the present invention may be practiced without some or all of these specific details. In other instances, well known process operations have not been described in detail in order not to unnecessarily obscure the present invention.

Figure 1:
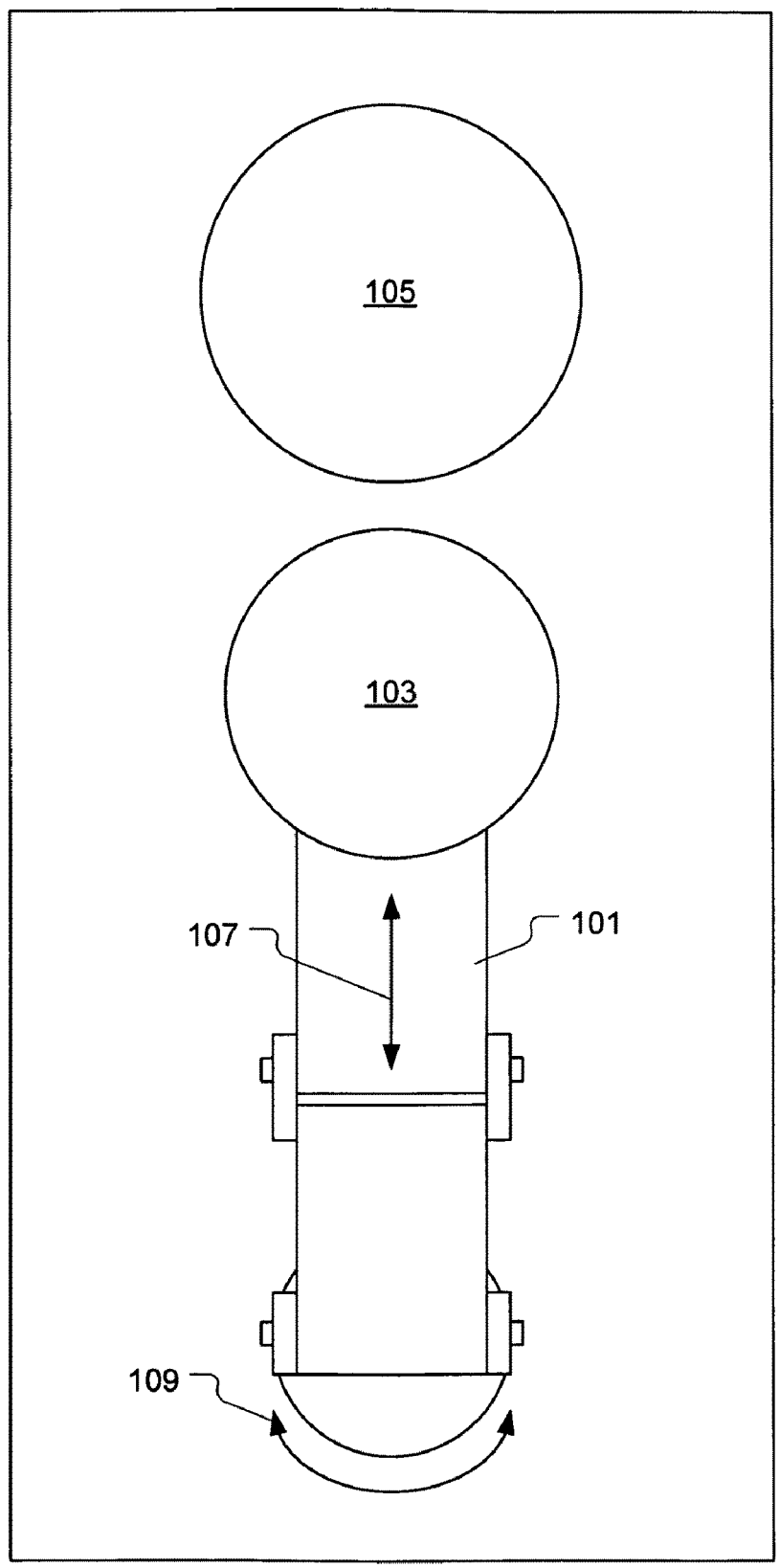
FIG. 1 shows a top view of a wafer handling mechanism relative to a chuck, in accordance with one embodiment of the present invention.

FIG. 1 shows a top view of a wafer handling mechanism 101 relative to a chuck 105, in accordance with one embodiment of the present invention. The wafer handling mechanism 101 is a robotic mechanism that provides for accurate movement and positioning of a wafer 103 relative to the chuck 105, so as to place the wafer 103 on the chuck 105 and remove the wafer 103 from the chuck 105. In one embodiment, the wafer handling mechanism 101 is defined to move the wafer 103 toward and away from the chuck 105, as indicated by arrow 107. Also, in this embodiment, the wafer handling mechanism 101 is defined to move the wafer 103 azimuthally about a rotational axis, as indicated by arrow 109.

It should be understood that the wafer handling mechanism 101 of FIG. 1 is provided by way of example and is not intended to limit the present invention in any way. Hence, in other embodiments the wafer handling mechanism 101 may differ in design and/or operation, so long as the wafer handling mechanism 101 is defined to place the wafer 103 on the chuck 105 in a precise and controllable manner. For example, in one embodiment, the wafer handling mechanism 101 provides for positioning of the wafer 103 relative to the chuck 105 through programming of coordinates by way of a computer system.

Figure 2:
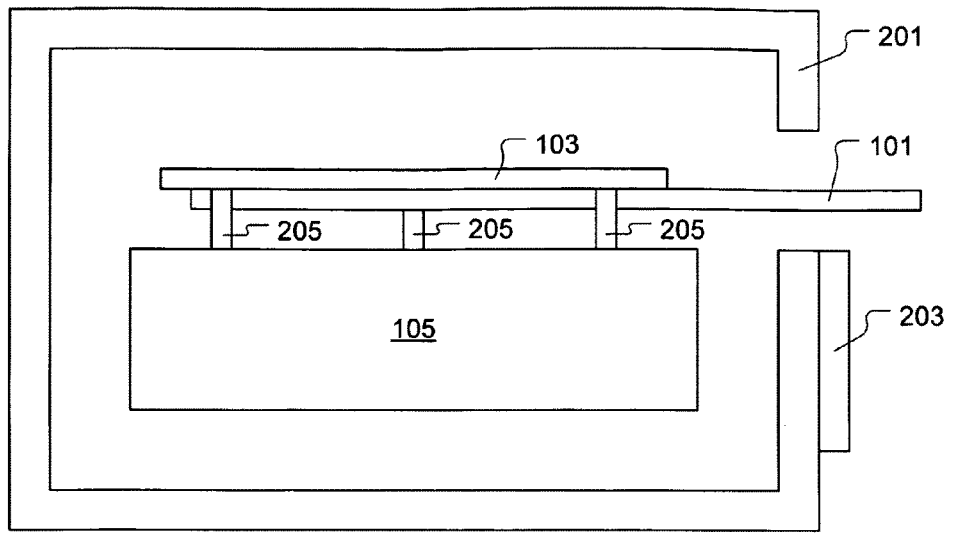
FIG. 2 shows a cross-section view of a wafer processing chamber, in accordance with one embodiment of the present invention.

FIG. 2 shows a cross-section view of a wafer processing chamber 201, in accordance with one embodiment of the present invention. The chamber 201 includes a moveable door 203 through which the wafer 103 can travel by way of the wafer handling mechanism 101. The chuck 105 is disposed within the chamber 201 to receive, support, and hold the wafer 103 during a wafer processing operation. In the exemplary embodiment of FIG. 2, the chuck 105 is defined to include a number of lifting pins 205 to facilitate placement of the wafer 103 on the chuck 105 and removal of the wafer 103 from the chuck 105. In this embodiment, the wafer handling mechanism 101 and lifting pins 205 are cooperatively defined to allow for placement of the wafer 103 on the lifting pins 205 when the lifting pins 205 are in a raised position. Then, the lifting pins 205 are lowered into the chuck 105 such that the wafer 103 is placed on the chuck. To remove the wafer 103, the lifting pins 205 are raised so as to lift the wafer 103 to a vertical position at which the wafer handling mechanism 101 can retrieve the wafer 103.

It should be appreciated that a positioning accuracy of wafer handling mechanism 101 determines a positioning accuracy of the wafer 103 on the chuck 105. Furthermore, it should be understood that the chamber 201 configuration of FIG. 2 is provided by way of example and is not intended to limit the present invention in any way. Therefore, positioning of the wafer 103 on the chuck 105 by way of the precise and controllable wafer handling mechanism 101 can be implemented with many other types of wafer processing equipment that utilize the chuck 105 to receive, support, and hold the wafer 103.

Figure 3:
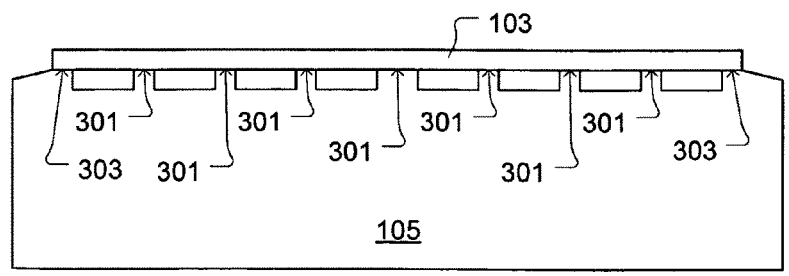
FIG. 3 shows a cross-section of the chuck, in accordance with one embodiment of the present invention.

FIG. 3 shows a cross-section of the chuck 105, in accordance with one embodiment of the present invention. The chuck 105 is defined to include a number of support features 301 and 303 defined to contact a surface of the wafer 103 when placed upon the chuck 105. More specifically, in the exemplary embodiment of FIG. 3, the support features 301 are defined as mesa-type structures of substantially uniform height that are distributed over the chuck 105 to support the wafer 103. Also, the support feature 303 represents an edge seal defined as a raised ring structure to support the periphery of the wafer 103. A height of the support feature 303 is substantially equivalent to the uniform height of the support features 301.

Figure 4:
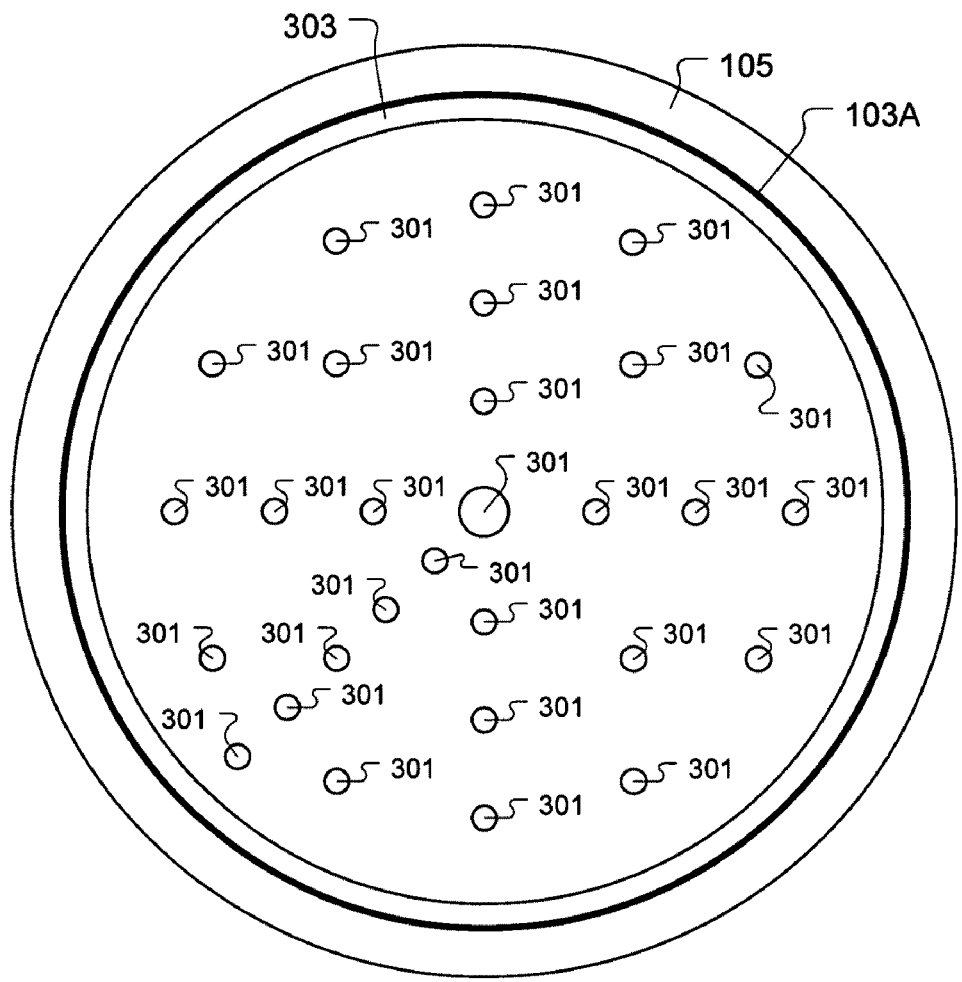
FIG. 4 shows a top view of the exemplary chuck of FIG. 3, in accordance with one embodiment of the present invention.

FIG. 4 shows a top view of the exemplary chuck 105 of FIG. 3, in accordance with one embodiment of the present invention. A periphery 103A of the wafer 103 is delineated to indicate placement of the wafer 103 on the chuck 105. In one embodiment, the chuck 105 is an electrostatic chuck defined to apply a chucking force to the wafer 103 through electrostatic attraction of the wafer 103 toward the chuck 105. It should be appreciated that the support features 301 are distributed across the chuck 105 to provide sufficiently uniform backside support of the wafer 103 in exposure to the chucking force.

When the chucking force is applied to the wafer 103, a defect pattern is created on the surface of the wafer in contact with the chuck 105. More specifically, a defect pattern is created by the support features 301 and 303 of the chuck 105 that contact the wafer 103. The defect pattern may include defects created in the wafer surface, particulates transferred to the wafer surface, or a combination thereof. For example, a defect may take the form of a divot or any other form of irregular feature relative to the wafer surface condition prior to chucking. Also, by way of example, particulates may take the form of flakes, particles, or any other form of foreign object present on the wafer surface.

Figure 5:
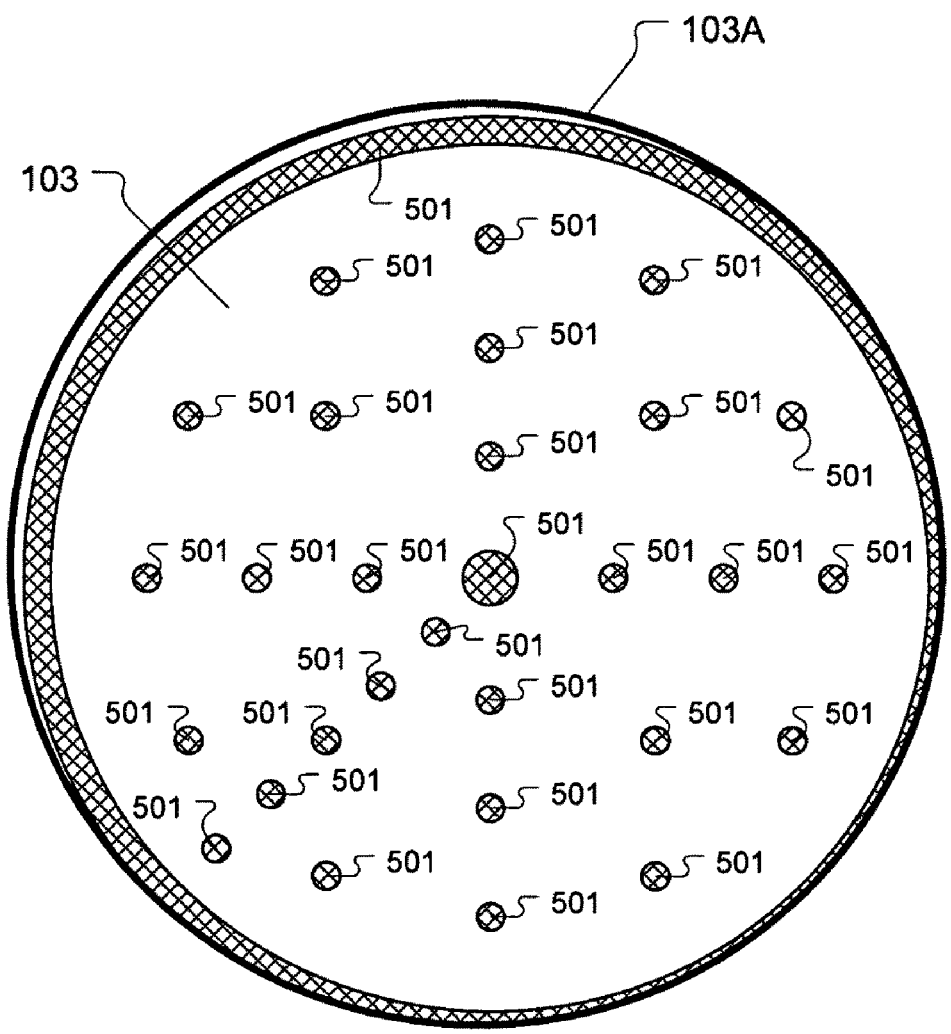
FIG. 5 shows the surface of the wafer having contacted the chuck with a corresponding defect pattern transferred thereon, in accordance with one embodiment of the present invention.

FIG. 5 shows the surface of the wafer 103 having contacted the chuck 105 with a corresponding defect pattern 501 transferred thereon, in accordance with one embodiment of the present invention. The defect pattern 501 transferred to the wafer 103 can be acquired by using a defect metrology tool to detect and map the defects present on the wafer 103. The defect metrology tool can be essentially any type of device defined to detect and map irregularities on a wafer surface. Example defect metrology tools include models KLA SP1 and KLA SP2 manufactured by KLA, Inc. It should be understood, however, that many different types of defect metrology tools can be utilized in conjunction with the present invention, so long as the defect metrology tool is capable of detecting and mapping defects of sufficiently small size with a sufficiently high accuracy. In one exemplary embodiment, the defect metrology tool is capable of detecting particles as small as 45 nanometers. However, the present invention can also be implemented with larger size defect detection capability.

The support features 301/303 of the chuck 105 that contact the wafer 103 are defined on the chuck 105 with tightly controlled tolerances and can be indexed to a center coordinate of the chuck 105, i.e., a center coordinate of a wafer receiving area of the chuck 105. Therefore, the spatial position of the support features 301/303 of the chuck 105 can be used to identify the center coordinate of the chuck 105. As few as two support features can be used to determine the center coordinate of the chuck 105. However, more support features may provide easier or more accurate identification of the center coordinate of the chuck 105.

Because the center coordinate of the chuck 105 can be determined from the spatial position of the support features 301/303 of the chuck 105, it follows that the center coordinate of the chuck 105 within a coordinate system of the wafer 103 can be determined from the defect pattern 501 transferred to the wafer 103 by the support features 301/303 of the chuck 105. Additionally, once the center coordinate of the chuck 105 is determined within the coordinate system of the wafer 103, the offset of the center coordinate of the chuck 105 from the center of the wafer 103 can be determined. Then, this offset can be used to adjust a placement of the wafer 103 on the chuck 105 so as to align the center of the wafer 103 to the center coordinate of the chuck 105.

The present invention includes an analysis procedure/module defined to determine the center coordinate of the chuck within the wafer coordinate system based on the defect pattern, i.e., defect map, representing defects transferred to the surface of the wafer by the support features of the chuck. The analysis procedure/module is further defined to determine the offset between the center coordinate of the chuck and the center of the wafer. The analysis procedure/module provides for definition of an inclusion region that spatially encloses the support features of the chuck.

Figure 6:
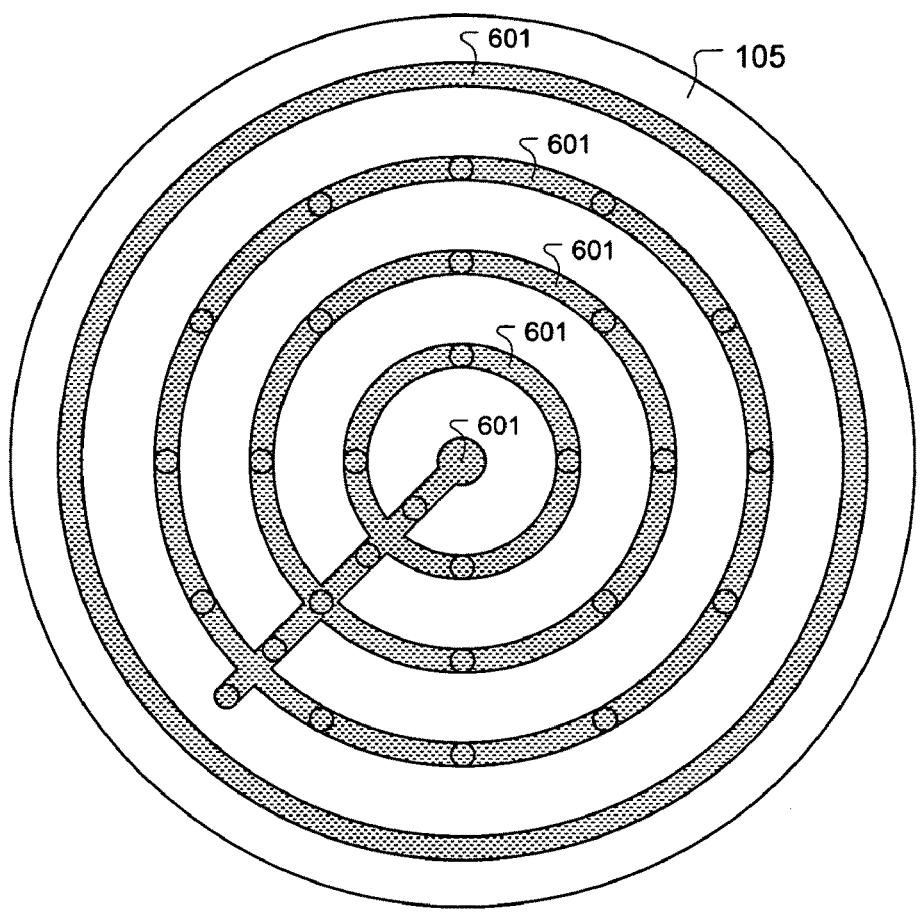
FIG. 6 shows an inclusion region defined to spatially enclose the support features of the chuck, in accordance with one embodiment of the present invention.

FIG. 6 shows an inclusion region 601 defined to spatially enclose the support features 301 and 303 of the chuck 105, in accordance with one embodiment of the present invention. The inclusion region 601 is defined to geometrically encompass the support features 301/303 of the chuck 105 that will contribute to the defect pattern 501 transferred to the wafer 103 during the chucking operation. Because the inclusion region 601 corresponds to the support features 301/303 of the chuck 105, the center coordinate of the chuck 105 within the wafer coordinate system can be derived from the position of the inclusion region 601 when the inclusion region 601 is positioned to enclose the defects transferred to the wafer 103 by the support features 301/303 of the chuck 105. To find the position of the inclusion region 601 that encloses the defects transferred to the wafer 103 by the support features 301/303 of the chuck 105, the inclusion region 601 is scanned over the defect metrology data to determine a maximum inclusion position at which the number of defects within the inclusion region 601 is maximized.

Figure 7A:
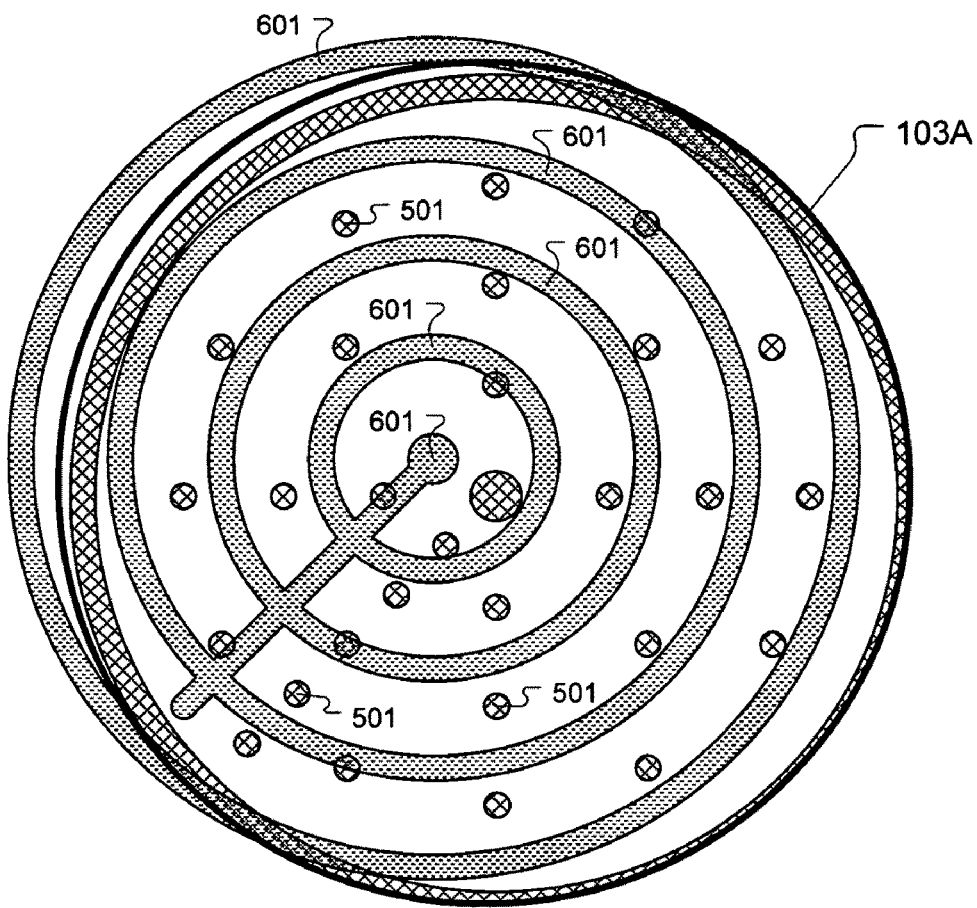
FIG. 7A shows the inclusion region at a given scanning position over the defect pattern transferred to the wafer by the chuck, in accordance with one embodiment of the present invention.

FIG. 7A shows the inclusion region 601 at a given scanning position over the defect pattern 501 transferred to the wafer 103 by the chuck 105, in accordance with one embodiment of the present invention. In one embodiment, the inclusion region 601 is scanned over the defect pattern 501 in an orthogonal rasterized manner, i.e., raster scanned, so as to provide for evaluation of a number of defects that fall within the inclusion region 601 at a number of orthogonal grid points, i.e., raster scan locations, across the wafer 103. A maximum inclusion position of the inclusion region 601 corresponds to a position of the inclusion region 601 at which the number of defects therein is maximized.

Figure 7B:
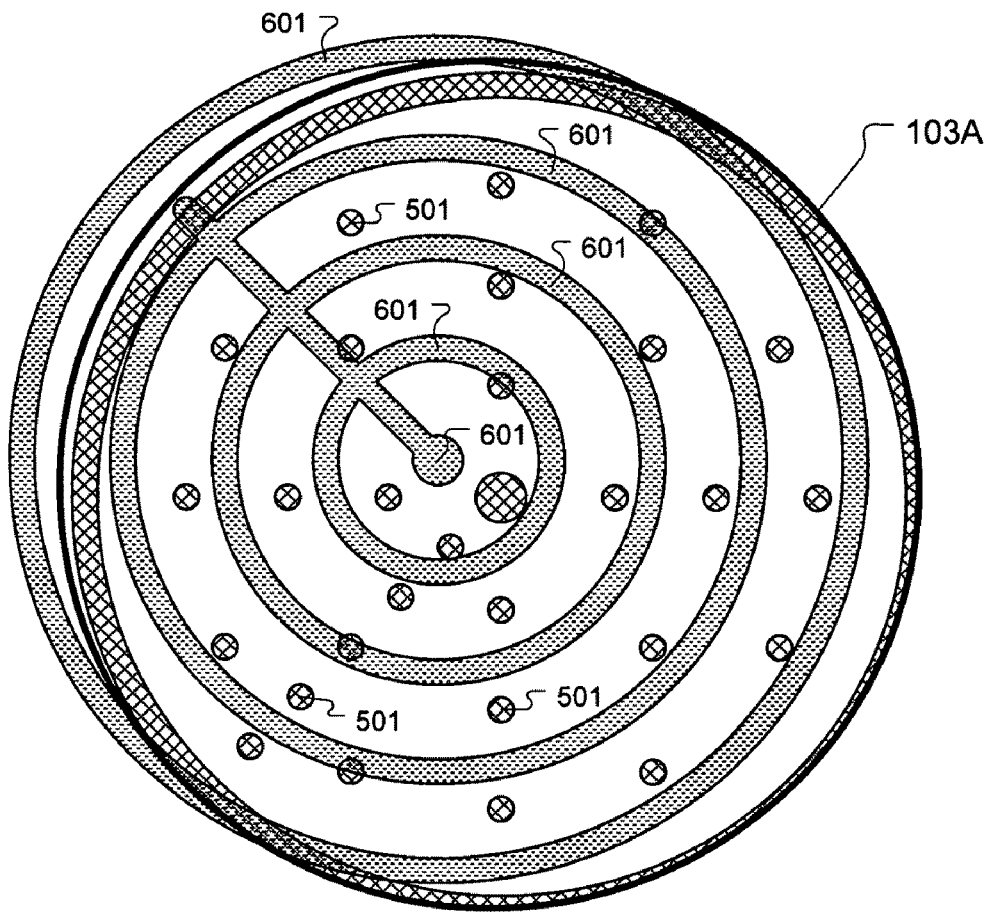
FIG. 7B shows the inclusion region at the same raster scan location of FIG. 7A, but at a different rotational orientation about the center coordinate of the chuck as referenced to the inclusion region.

In one embodiment, the support features 301/303 of the chuck 105 are defined in a non-symmetric manner about the center coordinate of the chuck 105, such that the maximum inclusion position of the inclusion region 601 has an azimuthal orientation component. The exemplary chuck 105 includes such non-symmetrically defined support features 301. In this embodiment, scanning of the inclusion region 601 over the defect pattern 501 includes rotation of the inclusion region 601 at each raster scan location. For example, FIG. 7B shows the inclusion region 601 at the same raster scan location of FIG. 7A, but at a different rotational orientation about the center coordinate of the chuck 105 as referenced to the inclusion region 601. In this manner, scanning of the inclusion region 601 over the defect pattern 501 provides for a determination of both a translational and rotational offset of the wafer 103 relative to the chuck 105.

Figure 7C:
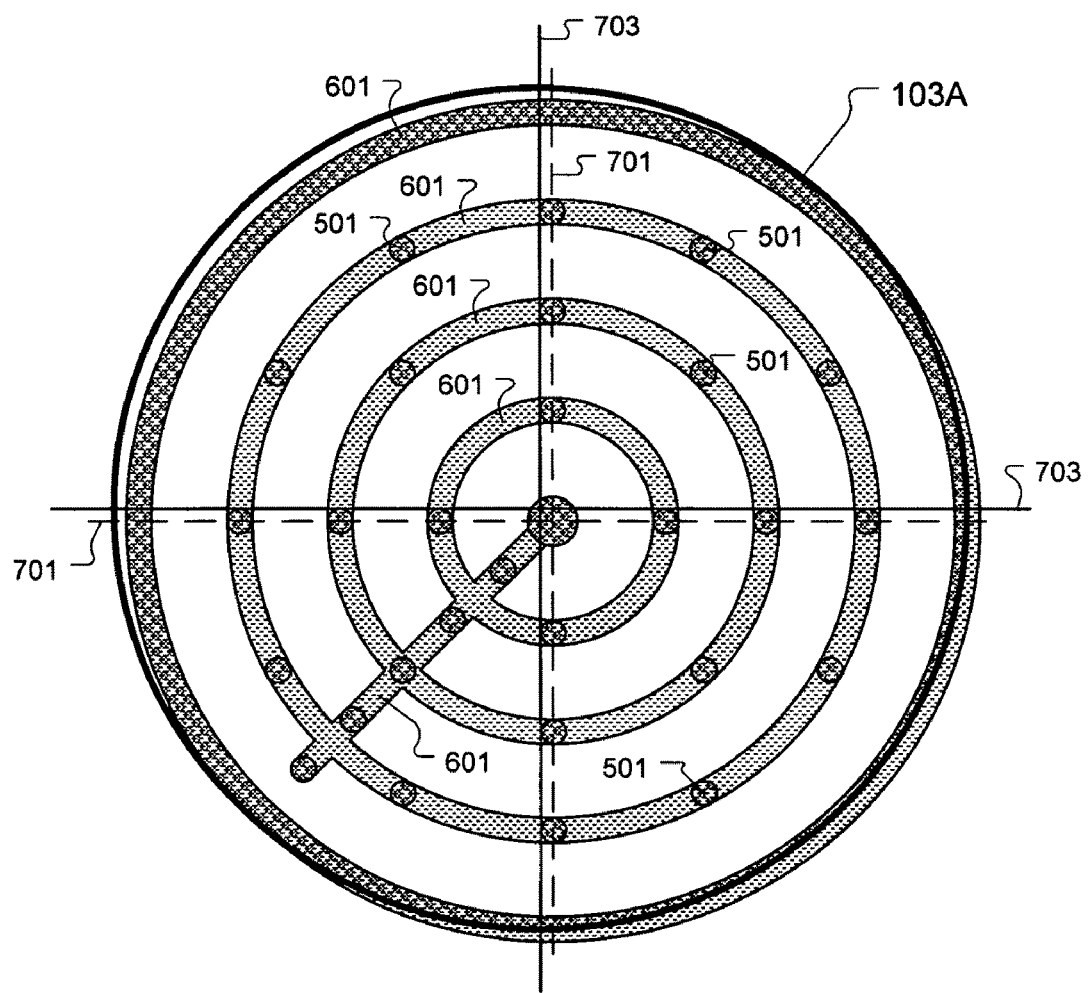
FIG. 7C shows the inclusion region at the maximum inclusion position, in accordance with one embodiment of the present invention.

FIG. 7C shows the inclusion region 601 at the maximum inclusion position, in accordance with one embodiment of the present invention. At the maximum inclusion position (and rotation, if applicable), the number of measured defects that fall within the inclusion region 601 is maximized. Although scanning of the inclusion region 601 over the defect pattern 501 has been described in physical terms herein for clarity, it should be understood that scanning of the inclusion region 601 over the defect pattern 501 can be performed entirely by computation based on a geometric definition of the inclusion region 601 and defect data, such as defect coordinates. The maximum inclusion position is determined within the coordinate system of the wafer 103. Therefore, based on the maximum inclusion position, the center coordinate of the chuck within the wafer coordinate system is known from the inclusion region 601 geometry. Consequently, the relationship between the center coordinate of the chuck and the center of the wafer during the chucking operation is known. Also, if the maximum inclusion position includes a rotational component, the azimuthal orientation of the wafer relative to the chuck during the chucking operation is known.

Figure 7D:
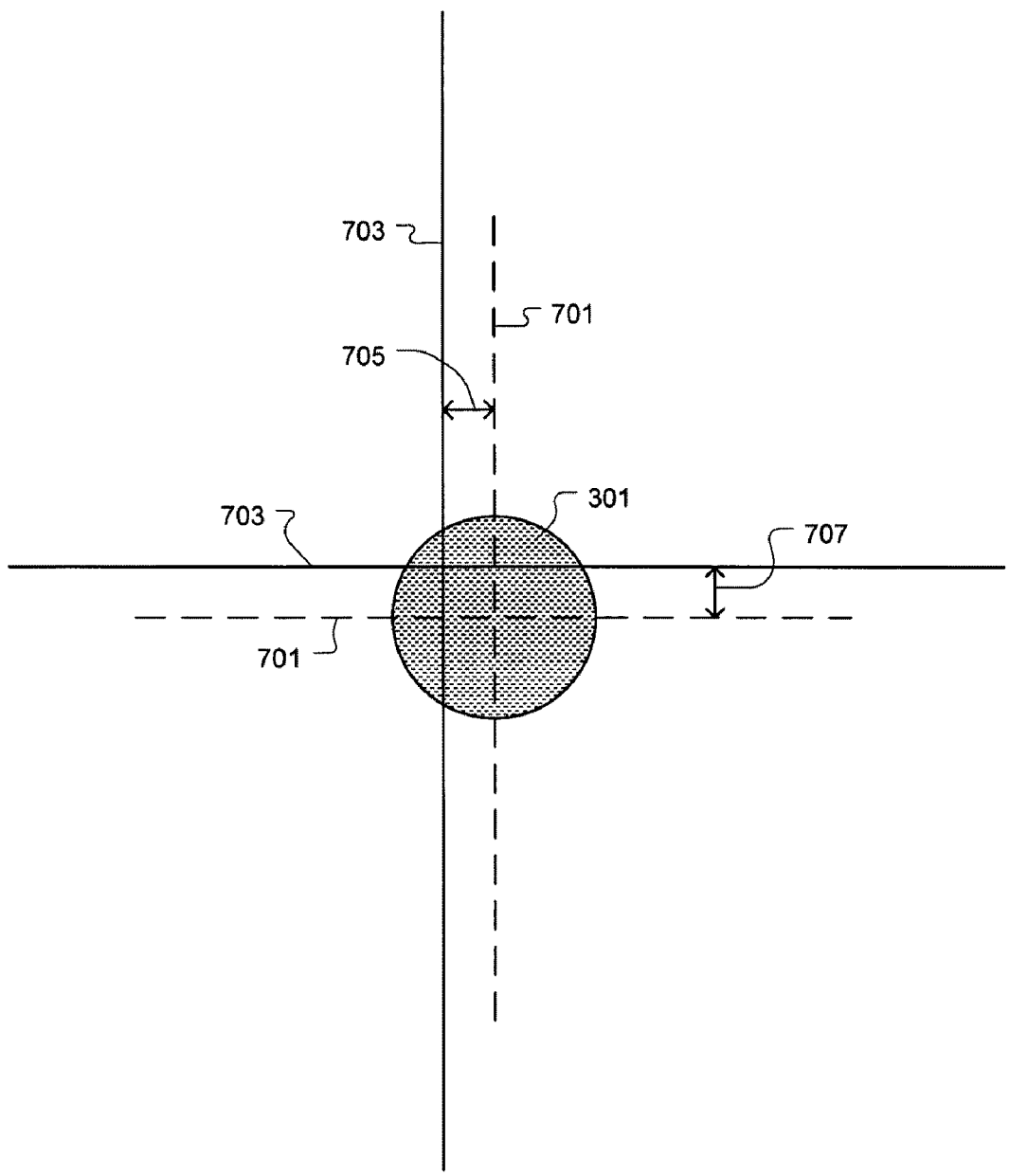
FIG. 7D shows the determined spatial relationship between the center coordinate of the chuck and the center of the wafer, in accordance with one embodiment of the present invention.

FIG. 7D shows the determined spatial relationship between the center coordinate of the chuck and the center of the wafer, in accordance with one embodiment of the present invention. The center coordinate of the chuck is shown by crosshairs 701. The center of the wafer is shown by crosshairs 703. The x-direction offset between the centers of the wafer and chuck is shown by arrow 705. The y-direction offset between the centers of the wafer and chuck is shown by arrow 707. The adjustment of the wafer handling mechanism 101 required to align the center of the wafer with the center coordinate of the chuck can be determined from the x-direction and y-direction offsets. The wafer handling mechanism 101 can then be adjusted/calibrated accordingly.

In one embodiment, the defect data as reported by the defect metrology tool may be spatially distorted in a systematic manner. For example, the reported defect coordinates may be radially biased about a center of the wafer. In this situation, a radial scale factor can be applied to the defect data to compensate for the spatial distortion introduced by the defect metrology tool. The radial scale factor essentially adjusts a radial position of the measured defects about the wafer center. In one embodiment, the radial scale factor is known and is applied to the defect data prior to scanning of the inclusion region 601 over the defect pattern 501. In another embodiment, the radial scale factor is not known. In this embodiment, the defect data of the defect pattern 501 is radially scaled at a number of inclusion region 601 scan locations to determine the appropriate radial scale factor to be applied. In one embodiment, the radial scale factor is determined using a low resolution analysis of the defect data. Then, the inclusion region 601 scan to find the maximum inclusion position is performed using a high resolution analysis of the defect data.

Figure 8:
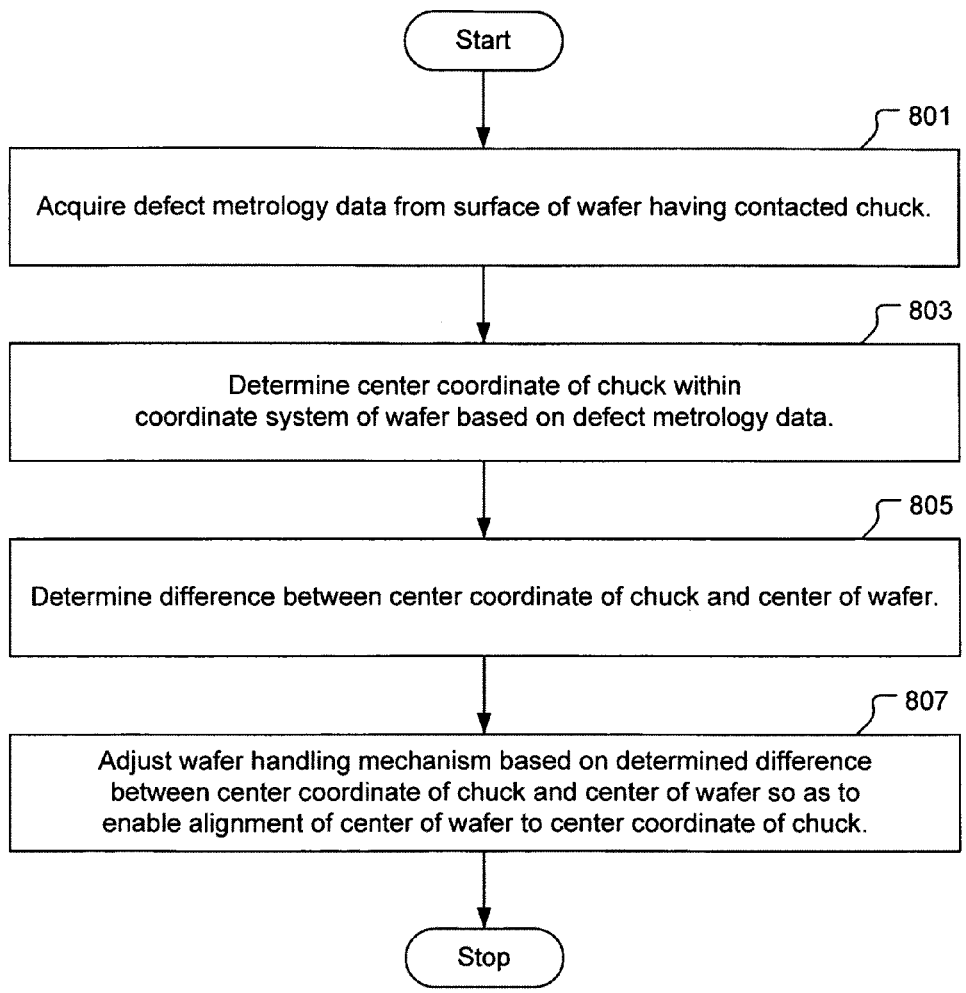
FIG. 8 shows a flowchart of a method for centering a wafer on a chuck, in accordance with one embodiment of the present invention.

FIG. 8 shows a flowchart of a method for centering a wafer on a chuck, in accordance with one embodiment of the present invention. The method includes an operation 801 for acquiring defect metrology data from a surface of the wafer having contacted the chuck. The defect metrology data can include defect location data, particulate location data, or a combination thereof, among other types of defect data. In one embodiment, acquiring the defect metrology data in operation 801 includes:

placing the wafer on the chuck, applying a chucking force to the wafer, removing the wafer from the chuck, and scanning the surface of the wafer having contacted the chuck with a defect metrology tool to detect and map defects on the surface of the wafer.

In one embodiment, the method also includes an operation for scaling the defect metrology data to compensate for a spatial distortion introduced by the defect metrology tool. The method also includes an operation 803 for determining a center coordinate of the chuck within a coordinate system of the wafer based on the defect metrology data. In one embodiment, determining the center coordinate of the chuck includes:

defining an inclusion region to enclose an expected spatial distribution of defect data resulting from chuck features defined to contact the surface of the wafer, spatially scanning the inclusion region over the defect metrology data to determine a maximum inclusion position at which a number of defects within the inclusion region is maximized, and determining the center coordinate of the chuck from the maximum inclusion position of the inclusion region.

In one embodiment, spatially scanning the inclusion region over the defect metrology data includes a raster scanning of the inclusion region over a wafer map of the defect metrology data. In this embodiment, a number of defects within the inclusion region is determined at a number of raster scan locations. Additionally, in one embodiment, the inclusion region is non-symmetric with respect to the center of the wafer. In this embodiment, spatially scanning the inclusion region over the defect metrology data also includes rotation of the inclusion region at each raster scan location.

The method further includes an operation 805 for determining a difference between the center coordinate of the chuck and a center of the wafer. The method also includes an operation 807 for adjusting a wafer handling mechanism based on the determined difference between the center coordinate of the chuck and the center of the wafer so as to enable alignment of the center of the wafer to the center coordinate of the chuck.

Figure 9:
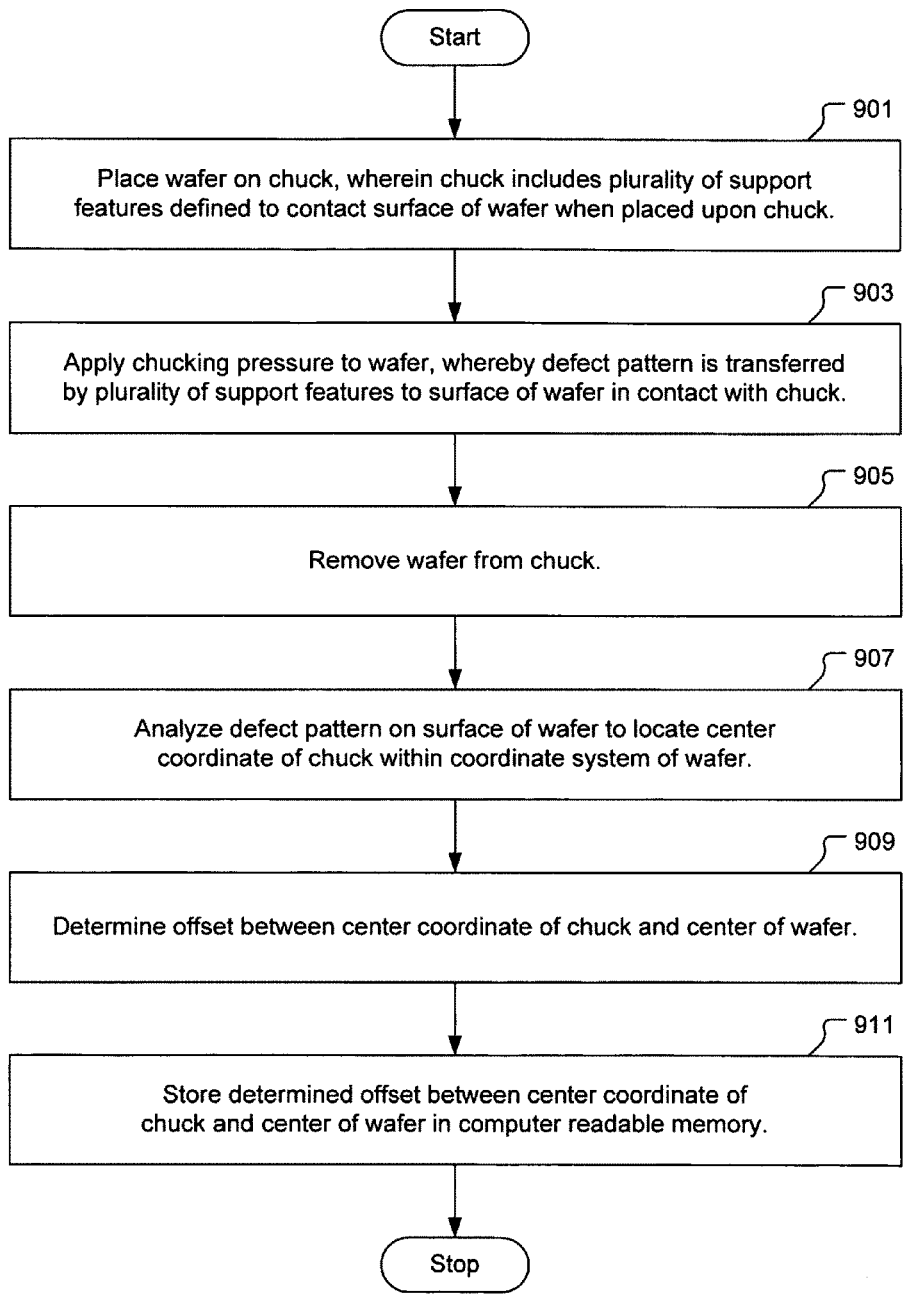
FIG. 9 shows a flowchart of a method for determining an offset of a wafer center from a chuck center, in accordance with one embodiment of the present invention.

FIG. 9 shows a flowchart of a method for determining an offset of a wafer center from a chuck center, in accordance with one embodiment of the present invention. The method includes an operation 901 for placing a wafer on a chuck. The chuck includes a plurality of support features defined to contact a surface of the wafer when placed upon the chuck. The method also includes an operation 903 for applying a chucking pressure to the wafer. Application of the chucking pressure to the wafer causes a defect pattern to be transferred by the plurality of support features to the surface of the wafer in contact with the chuck. The defect pattern can include physical defects on the surface of the wafer and/or particulate contaminants on the surface of the wafer, among other types of defects. It should be understood that a defect represents any form of irregularity on the wafer surface.

The method further includes an operation 905 for removing the wafer from the chuck. Then, an operation 907 is performed to analyze the defect pattern on the surface of the wafer to locate a center coordinate of the chuck within a coordinate system of the wafer. In one embodiment, analyzing the defect pattern on the surface of the wafer includes:

analyzing the surface of the wafer having contacted the chuck with a defect metrology tool to detect and map defects on the surface of the wafer, defining an inclusion region to enclose a spatial distribution of the plurality of support features defined to contact the surface of the wafer, spatially scanning the inclusion region over the defects as mapped on the surface of the wafer to determine a maximum inclusion position at which a number of defects within the inclusion region is maximized, and determining the center coordinate of the chuck from the maximum inclusion position of the inclusion region using a known spatial relationship between the plurality of support features and the center coordinate of the chuck.

In one embodiment, spatially scanning the inclusion region includes moving the inclusion region in a rasterized manner over the defects as mapped on the surface of the wafer, such that a number of defects within the inclusion region is determined at a number of raster scan locations. In one embodiment, the inclusion region is non-symmetric with respect to the center of the wafer. In this embodiment, spatially scanning the inclusion region over the defects as mapped on the surface of the wafer includes rotation of the inclusion region at each raster scan location.

The method continues with an operation 909 for determining an offset between the center coordinate of the chuck and a center of the wafer. An operation 911 is then performed to store the determined offset between the center coordinate of the chuck and the center of the wafer in a computer readable memory. It should be understood that placement of the wafer on the chuck in operation 901, application of the chucking pressure to the wafer in operation 903, and removal of the wafer from the chuck in operation 905 can be performed in accordance with normal operating procedures. Therefore, the wafer processing chamber within which the chuck resides does not need to be modified to determine the offset of the wafer center from the chuck center.

In view of the foregoing, it should be understood that the wafer should be defined to enable transfer of the defect pattern thereto without causing the transferred defect pattern to be obscured by pre-existing wafer defects or other characteristics. In one embodiment, a polished side of a wafer is contacted with the chuck to receive the defect pattern formed by the support features of the chuck. The polished side of the wafer provides a substantially clear canvas for receiving the defects caused by contact with support features of the chuck. The wafer can be essentially any type of wafer on which defects can be measured. For example, in one embodiment, the wafer is a reclaimed wafer. Additionally, in one embodiment, the surface of the chuck can be pre-treated with a coating, such as a silicon based film (e.g., AC3), before chucking the wafer to enhance transfer of defects to the wafer, and/or to suppress the occurrence of spurious defects unrelated to the desired support feature pattern to be transferred to the wafer during the chucking process. Furthermore, in one embodiment, a defect metrology tool is deployed to enable defect measurement of a backside of a process wafer in real-time as the process-wafer is removed from the processing chamber. In this embodiment, the backside defect data of the process wafer can be analyzed to enable wafer centering adjustment of the wafer handling mechanism in real-time.

Figure 10:
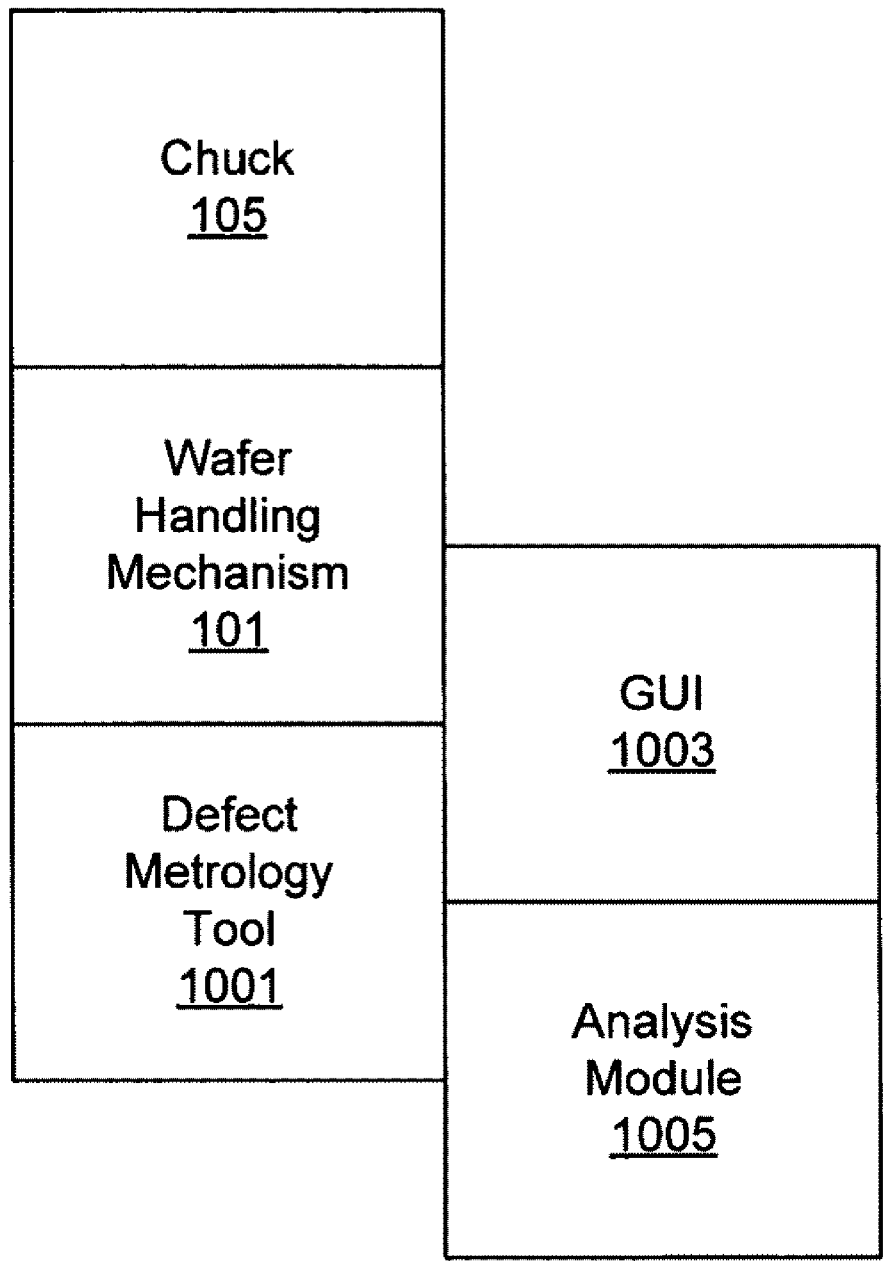
FIG. 10 shows a diagram of a system for centering a wafer on a chuck, in accordance with one embodiment of the present invention.

FIG. 10 shows a diagram of a system for centering a wafer on a chuck, in accordance with one embodiment of the present invention. The system includes the chuck 105. As previously discussed, the chuck 105 includes a plurality of support features defined to contact a surface of a wafer when positioned upon the chuck 105. The system also includes the wafer handling mechanism 101 defined to position the wafer on the chuck 105. The system also includes a defect metrology tool 1001 defined to detect and map defects on the surface of the wafer. The system further includes an analysis module 1005 defined to determine a center coordinate of the chuck within a wafer coordinate system based on a defect map generated by the defect metrology tool. The defect map represents defects transferred to the surface of the wafer by the plurality of support features of the chuck. The analysis module 1005 is further defined to determine an offset between the center coordinate of the chuck and a center of the wafer and store the determined offset in a computer readable memory.

The analysis module 1005 is further defined to provide for definition of an inclusion region that spatially encloses the plurality of support features of the chuck. The center coordinate of the chuck is derivable from a spatial position of the inclusion region. The analysis module 1005 is also defined to spatially scan the inclusion region over the defect map to determine a maximum inclusion position at which a number of defects within the inclusion region is maximized. The analysis module 1005 is further defined to determine the center coordinate of the chuck based on the determined maximum inclusion position of the inclusion region.

Additionally, in one embodiment, the system includes a graphical user interface (GUI) 1003 defined to render images and views associated with the wafer centering operation. For example, the GUI 1003 can be defined to render the defect map on an image of the wafer, render the determined maximum inclusion position of the inclusion region, render the determined center coordinate of the chuck, render the center of the wafer, and render the determined offset between the center coordinate of the chuck and the center of the wafer.

Figure 11:
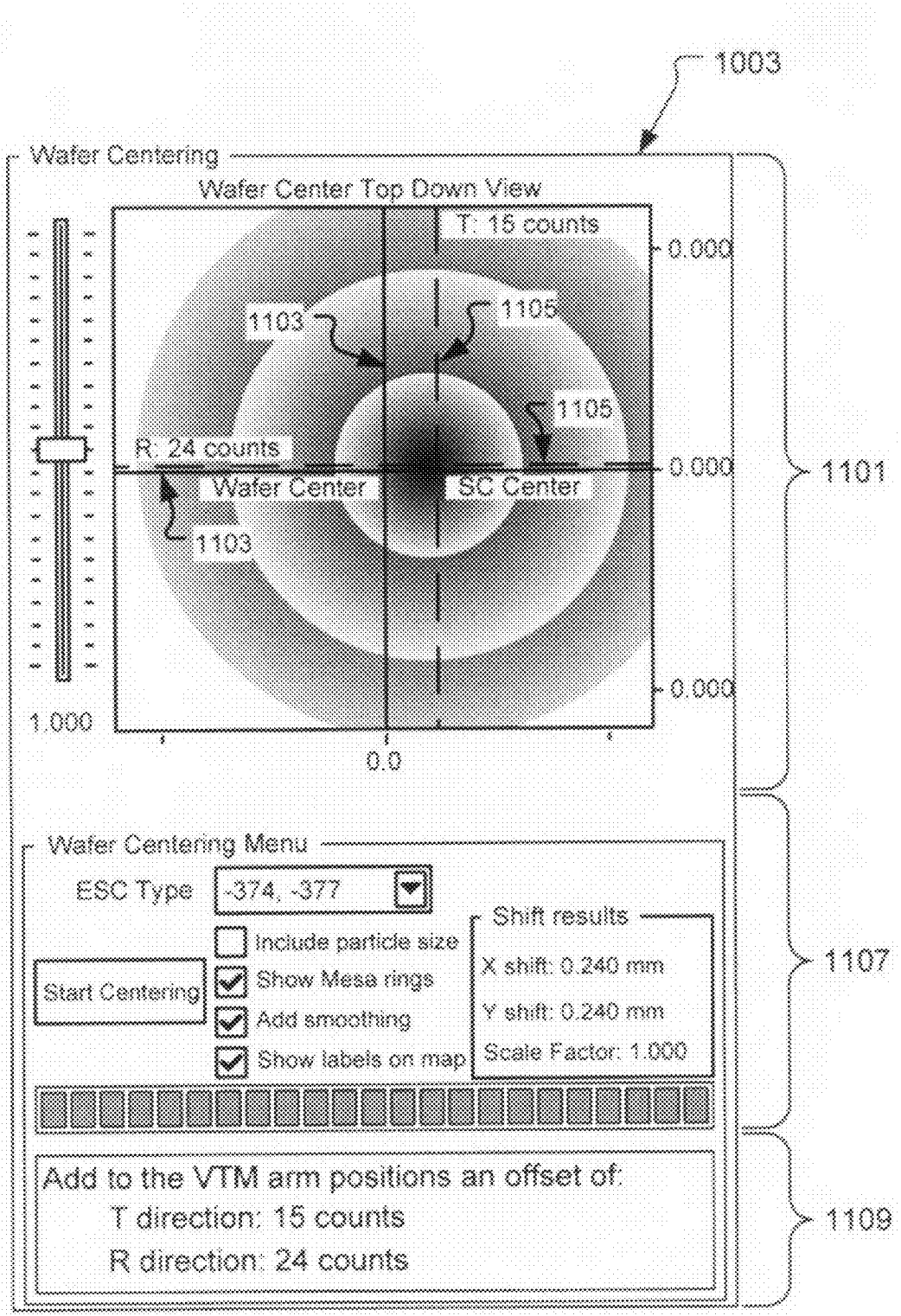
FIG. 11 shows an exemplary GUI, in accordance with one embodiment of the present invention.

FIG. 11 shows an exemplary GUI 1003, in accordance with one embodiment of the present invention. The GUI 1003 includes a window 1101 that displays a plot of the number of defects residing in the inclusion region as a function of raster scan location of the inclusion region. The window 1101 also includes crosshairs 1103 indicating the center of the wafer, and crosshairs 1105 indicating the center of the chuck as determined by the defect pattern on the wafer. The GUI 1003 also includes a region 1107 that provides a number of display controls for the window 1101 and wafer center-to-chuck center offset results ("Shift Results"). The GUI 1003 further includes a window 1109 that provides a set of calculated wafer handling mechanism adjustments required to align the wafer center to the chuck center. In the example of FIG. 11, the "T direction" adjustment corresponds to an azimuthal adjustment, such as indicated by arrow 109 of FIG. 1. Also, the "R direction" adjustment corresponds to a radius adjustment, such as indicated by arrow 107 of FIG. 1. Also, the "counts" represent incremental movements of stepper motors used to position the wafer handling mechanism. In one example, one count in the T direction may correspond to about 16 micrometers, and one count in the R direction may correspond to about 1 micrometer.

In one embodiment, the methods and system for centering a wafer on a chuck as described herein are capable of positioning the center of the wafer within approximately 0.002 inch of the center of the chuck. Additionally, it should be appreciated that the methods and system for centering a wafer on a chuck as described herein do not require hardware changes to existing wafer processing equipment and can be performed by operating the wafer processing equipment in normal operation mode.

With the above embodiments in mind, it should be understood that the present invention may employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations described herein that form part of the invention are useful machine operations. The invention also relates to a device or an apparatus for performing these operations. The apparatus may be specially constructed for the required purposes, or it may be a general-purpose computer selectively activated or configured by a computer program stored in the computer. In particular, various general-purpose machines may be used with computer programs written in accordance with the teachings herein, or it may be more convenient to construct a more specialized apparatus to perform the required operations.

The invention can also be embodied as computer readable code on a computer readable medium. The computer readable medium is any data storage device that can store data which can be thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. Additionally, the computer readable code comprising the present invention may be stored on multiple computer readable medium devices distributed over a network of coupled computer systems so that the computer readable code is stored and executed in a distributed fashion.

While this invention has been described in terms of several embodiments, it will be appreciated that those skilled in the art upon reading the preceding specifications and studying the drawings will realize various alterations, additions, permutations and equivalents thereof. Therefore, it is intended that the present invention includes all such alterations, additions, permutations, and equivalents as fall within the true spirit and scope of the invention.

What is claimed is:

1. A method for centering a wafer on a chuck, comprising:
   acquiring defect metrology data from a surface of the wafer having contacted the chuck;
   determining a center coordinate of the chuck within a coordinate system of the wafer based on the defect metrology data;
   determining a difference between the center coordinate of the chuck and a center of the wafer; and
   adjusting a wafer handling mechanism based on the determined difference between the center coordinate of the chuck and the center of the wafer so as to enable alignment of the center of the wafer to the center coordinate of the chuck.

2. A method for centering a wafer on a chuck as recited in claim 1, wherein the defect metrology data includes defect location data, particulate location data, or a combination of both defect location data and particulate location data.

3. A method for centering a wafer on a chuck as recited in claim 1, wherein acquiring defect metrology data includes:
   placing the wafer on the chuck,
   applying a chucking force to the wafer,
   removing the wafer from the chuck, and
   scanning the surface of the wafer having contacted the chuck with a defect metrology tool to detect and map defects on the surface of the wafer.

4. A method for centering a wafer on a chuck as recited in claim 3, further comprising:
scaling the defect metrology data to compensate for a spatial distortion introduced by the defect metrology tool.

5. A method for centering a wafer on a chuck as recited in claim 1, wherein determining the center coordinate of the chuck includes:
defining an inclusion region to enclose an expected spatial distribution of defect data resulting from chuck features defined to contact the surface of the wafer, wherein a spatial relationship between the chuck features defined to contact the surface of the wafer and the center coordinate of the chuck is known,
spatially scanning the inclusion region over the defect metrology data to determine a maximum inclusion position at which a number of defects within the inclusion region is maximized, and
determining the center coordinate of the chuck from the maximum inclusion position of the inclusion region.

6. A method for centering a wafer on a chuck as recited in claim 5, wherein spatially scanning the inclusion region over the defect metrology data includes a raster scanning of the inclusion region over a wafer map of the defect metrology data, such that a number of defects within the inclusion region is determined at a number of raster scan locations.

7. A method for centering a wafer on a chuck as recited in claim 6, wherein the inclusion region is non-symmetric with respect to the center of the wafer, and wherein spatially scanning the inclusion region over the defect metrology data also includes rotation of the inclusion region at each raster scan location.

8. A method for determining an offset of a wafer center from a chuck center, comprising:
placing a wafer on a chuck, wherein the chuck includes a plurality of support features defined to contact a surface of the wafer when placed upon the chuck;
applying a chucking pressure to the wafer, whereby a defect pattern is transferred by the plurality of support features to the surface of the wafer in contact with the chuck;
removing the wafer from the chuck;
analyzing the defect pattern on the surface of the wafer to locate a center coordinate of the chuck within a coordinate system of the wafer;
determining an offset between the center coordinate of the chuck and a center of the wafer; and
storing the determined offset between the center coordinate of the chuck and the center of the wafer in a computer readable memory.

9. A method for determining an offset of a wafer center from a chuck center as recited in claim 8, wherein placement of the wafer on the chuck, application of the chucking pressure to the wafer, and removal of the wafer from the chuck are performed in accordance with normal operating procedures.

10. A method for determining an offset of a wafer center from a chuck center as recited in claim 8, wherein the defect pattern includes physical defects on the surface of the wafer, particulate contaminants on the surface of the wafer, or a combination of both physical defects and particulate contaminants on the surface of the wafer.

11. A method for determining an offset of a wafer center from a chuck center as recited in claim 8, wherein analyzing the defect pattern on the surface of the wafer includes:
analyzing the surface of the wafer having contacted the chuck with a defect metrology tool to detect and map defects on the surface of the wafer,
defining an inclusion region to enclose a spatial distribution of the plurality of support features defined to contact the surface of the wafer,
spatially scanning the inclusion region over the defects as mapped on the surface of the wafer to determine a maximum inclusion position at which a number of defects within the inclusion region is maximized, and
determining the center coordinate of the chuck from the maximum inclusion position of the inclusion region using a known spatial relationship between the plurality of support features and the center coordinate of the chuck.

12. A method for determining an offset of a wafer center from a chuck center as recited in claim 11, further comprising:
radially scaling the mapped defects relative to the center of the wafer to compensate for a spatial distortion introduced by the defect metrology tool.

13. A method for determining an offset of a wafer center from a chuck center as recited in claim 11, wherein spatially scanning the inclusion region includes moving the inclusion region in a rasterized manner over the defects as mapped on the surface of the wafer, such that a number of defects within the inclusion region is determined at a number of raster scan locations.

14. A method for determining an offset of a wafer center from a chuck center as recited in claim 13, wherein the inclusion region is non-symmetric with respect to the center of the wafer, and wherein spatially scanning the inclusion region includes rotation of the inclusion region at each raster scan location.

15. A system for centering a wafer on a chuck, comprising:
a chuck including a plurality of support features defined to contact a surface of a wafer when positioned upon the chuck;
a wafer handling mechanism defined to position the wafer on the chuck;
a defect metrology tool defined to detect and map defects on the surface of the wafer; and
an analysis module defined to determine a center coordinate of the chuck within a wafer coordinate system based on a defect map generated by the defect metrology tool representing defects transferred to the surface of the wafer by the plurality of support features of the chuck, wherein the analysis module is further defined to determining an offset between the center coordinate of the chuck and a center of the wafer and store the determined offset in a computer readable memory.

16. A system for centering a wafer on a chuck as recited in claim 15, wherein some of the plurality of support features are defined as mesa structures and are distributed in a concentric circular pattern about the center coordinate of the chuck.

17. A system for centering a wafer on a chuck as recited in claim 15, wherein the plurality of support features include a number of support features that are defined at non-symmetric locations about the center coordinate of the chuck.

18. A system for centering a wafer on a chuck as recited in claim 15, wherein the chuck is defined as an electrostatic chuck.

19. A system for centering a wafer on a chuck as recited in claim 15, wherein the analysis module provides for definition of an inclusion region that spatially encloses the plurality of support features of the chuck, such that the center coordinate of the chuck is derivable from a spatial position of the inclusion region, and
   wherein the analysis module is defined to spatially scan the inclusion region over the defect map to determine a maximum inclusion position at which a number of defects within the inclusion region is maximized, and
   wherein the analysis module is defined to determine the center coordinate of the chuck based on the determined maximum inclusion position of the inclusion region.

20. A system for centering a wafer on a chuck as recited in claim 19, further comprising:
   a graphical user interface defined to render the defect map on an image of the wafer, render the determined maximum inclusion position of the inclusion region, render the determined center coordinate of the chuck, render the center of the wafer, and render the determined offset between the center coordinate of the chuck and the center of the wafer.

* * * * *